US00PP20731P2

(12) United States Plant Patent
Mowrey et al.

(10) Patent No.: US PP20,731 P2
(45) Date of Patent: Feb. 9, 2010

(54) STRAWBERRY PLANT NAMED 'DRISSTRAWELEVEN'

(50) Latin Name: *Fragaria×ananassa*
Varietal Denomination: DrisStrawEleven

(75) Inventors: Bruce D. Mowrey, Watsonville, CA (US); Joanne F. Coss, Watsonville, CA (US); Martin P. Madesko, Watsonville, CA (US); Philip J. Stewart, Watsonville, CA (US); Matthew P. Wilson, San Luis Obispo, CA (US); Michael D. Ferguson, Moorpark, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 12/291,629

(22) Filed: Nov. 12, 2008

(51) Int. Cl.
*A01H 5/00* (2006.01)

(52) U.S. Cl. ..... Plt./209

(58) Field of Classification Search ..... Plt./209
See application file for complete search history.

*Primary Examiner*—Annette H Para
(74) *Attorney, Agent, or Firm*—Jondle & Associates, P.C.

(57) ABSTRACT

This invention relates to a new and distinct cultivar of strawberry plant named 'DrisStrawEleven'. The new cultivar is primarily characterized by its medium-sized, conical-shaped fruit having a strong sweetness and medium acidity and moderate resistance to Strawberry Moftle Virus, is disclosed.

3 Drawing Sheets

Genus and species: *Fragaria×ananassa.*
Variety denomination: 'DrisStrawEleven'.

BACKGROUND OF THE NEW PLANT

The present invention relates to a new and distinct strawberry cultivar designated 'DrisStrawEleven' and botanically known as *Fragaria×ananassa*. This new strawberry cultivar was discovered in Monterey, Calif. in summer 2004 and originated from a cross between the proprietary female parent '122J81' (unpatented) and the proprietary male parent '111H69' (unpatented). The original seedling of the new cultivar was first asexually propagated at a nursery in Shasta County, Calif.

'DrisStrawEleven' was subsequently asexually propagated in Shasta County, Calif. and underwent further testing at nurseries in Monterey and San Luis Obispo, Calif. for five years. The present invention has been found to retain its distinctive characteristics through successive asexual propagations.

DESCRIPTION OF THE PHOTOGRAPHS

The accompanying color photographs show typical specimens of the new cultivar at various stages of development as nearly true as it is possible to make in color reproductions. The photographs were taken from plants that were 7 months-old.

DESCRIPTION OF THE NEW CULTIVAR

Figure 1:
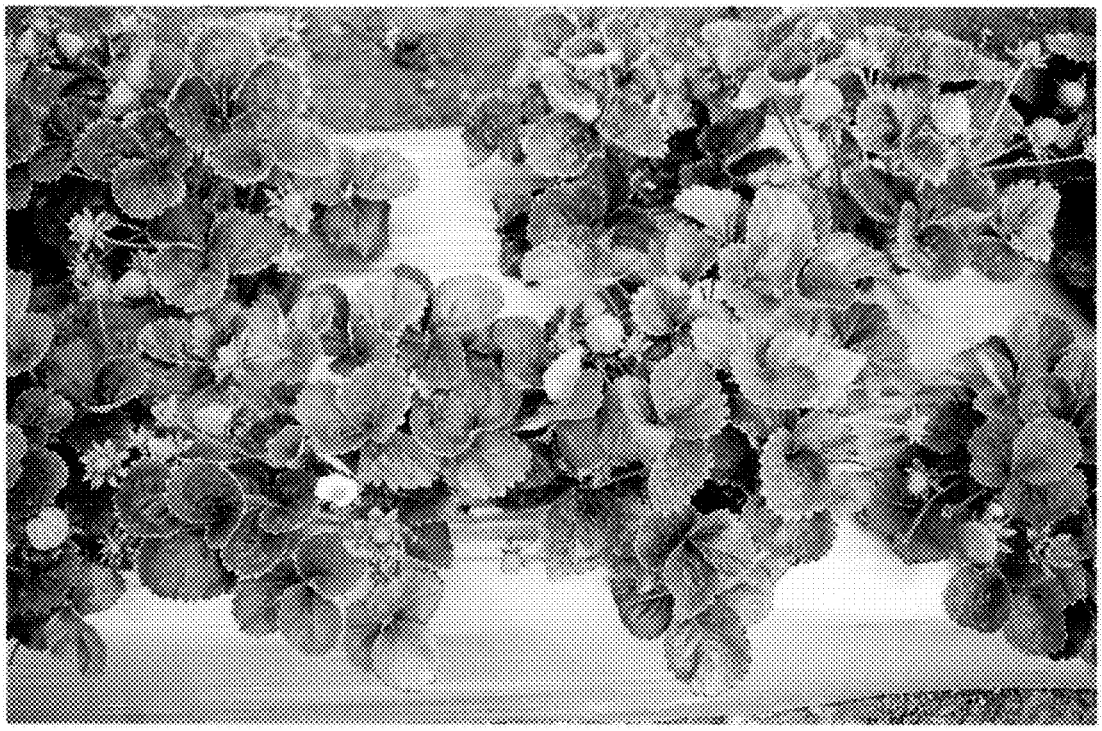
FIG. 1 shows overall plant habit including fruit at various stages of development.
Figure 2:
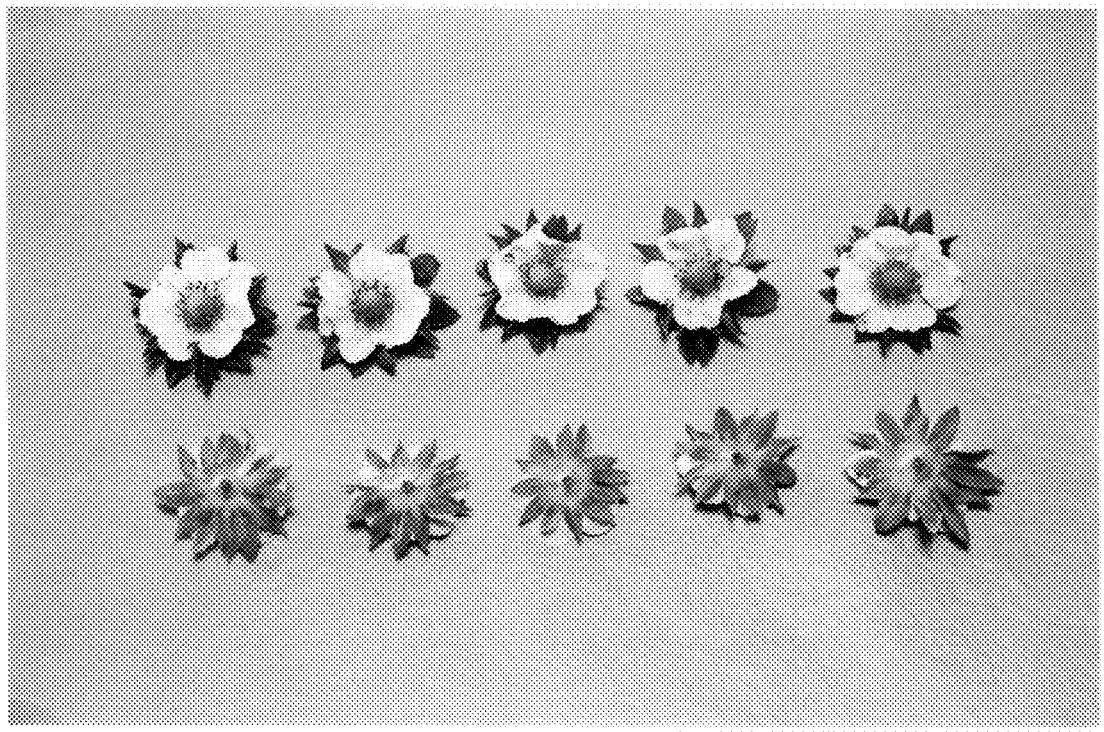
FIG. 2 shows the upper and lower surfaces of several of the flowers.
Figure 3:
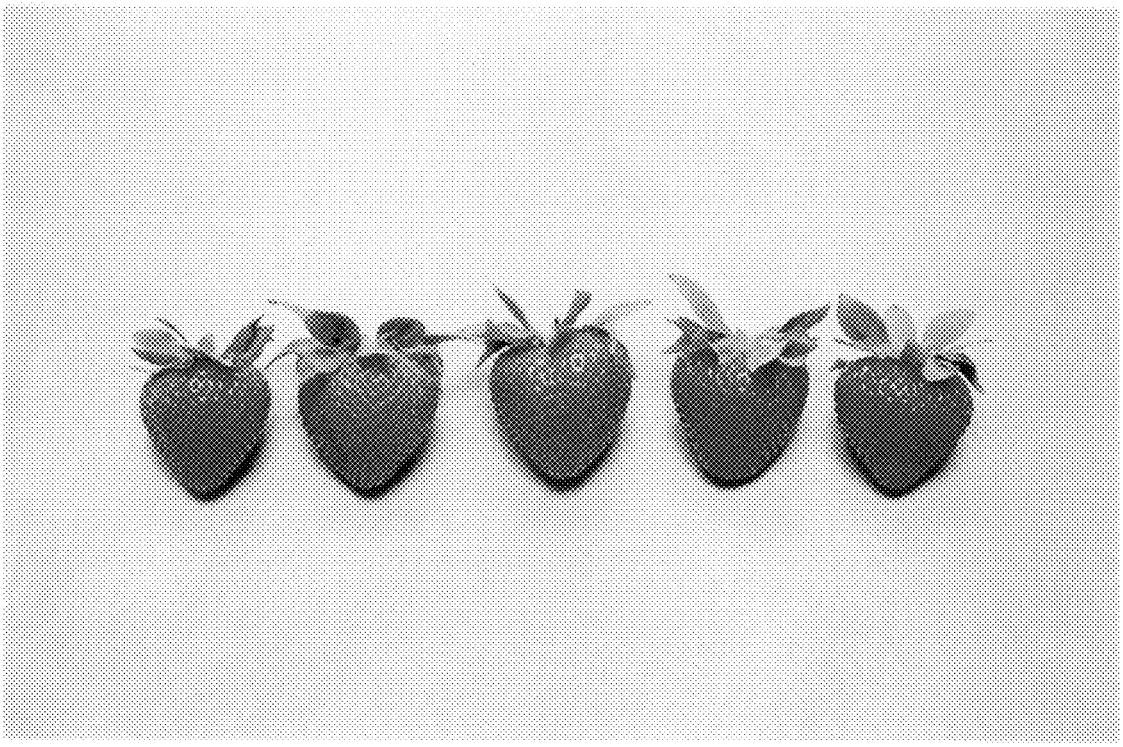
FIG. 3 shows the whole fruit.
Figure 4:
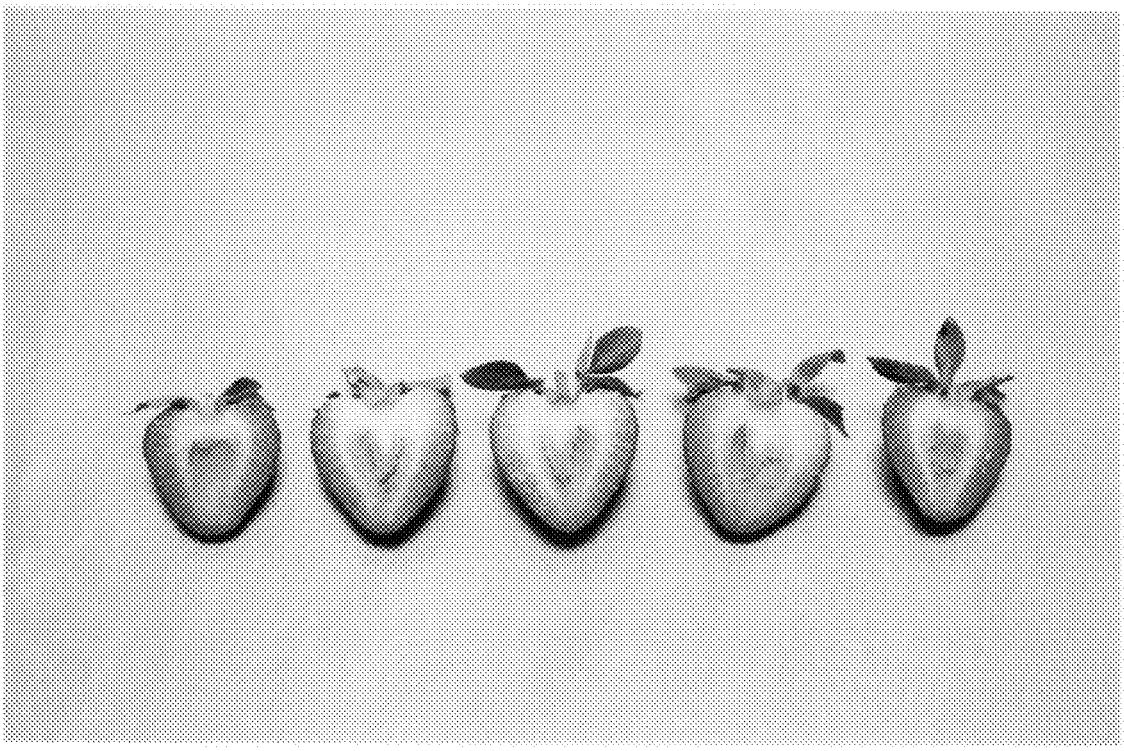
FIG. 4 shows the fruit in longitudinal cross-section.
Figure 5:
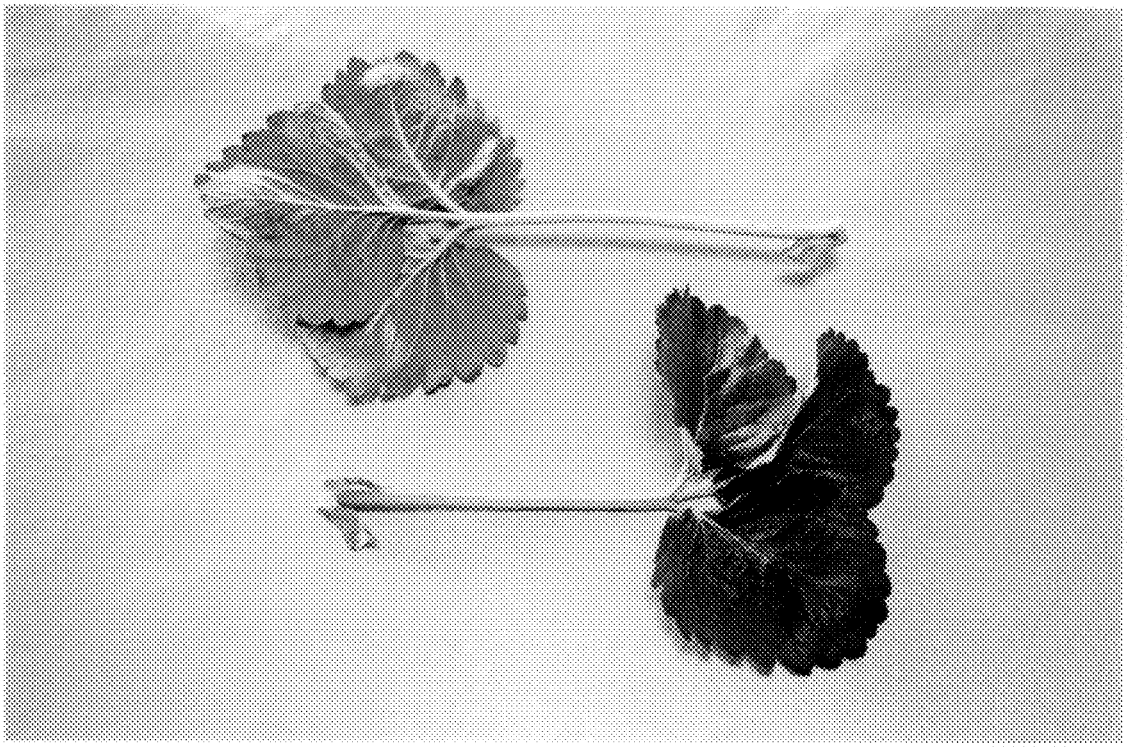
FIG. 5 shows the upper and lower surfaces of the leaves at the three leaf stage.

The following description of 'DrisStrawEleven' is based on observations taken in Monterey and San Luis Obispo, Calif. from 2004–2008. This description is in accordance with UPOV terminology. Color designations, color descriptions, and other phenotypical descriptions may deviate from the stated values and descriptions depending upon variation in environmental, seasonal, climatic and cultural conditions. 'DrisStrawEleven' has not been observed under all possible environmental conditions. The botanical description of 'DrisStrawEleven' was taken from 7 month-old plants and the botanical descriptions of 'Driscoll Lanai' and 'San Juan' were taken from 7 month-old plants. Color terminology follows The Royal Horticultural Society Colour Chart, London (R.H.S.) (2001).

DETAILED BOTANICAL DESCRIPTION

Table 1 shows selected plant characteristics of the new variety compared with plant characteristics of 'Driscoll Lanai' (U.S. Plant Pat. No. 15,145) and 'San Juan' (U.S. Plant Pat. No. 12,899). Plant characteristics include plant habit, terminal leaflet margin profile, insertion of achenes and fruit production.

TABLE 1

| Characteristic | 'DrisStrawEleven' | 'Driscoll Lanai' | 'San Juan' |
|---|---|---|---|
| Plant habit | Upright | Flat globose | Between upright and flat globose |
| Terminal leaflet margin profile | Cupped | Revolute | Revolute |
| Insertion of achenes | Level with surface | Above surface | Below surface |
| Fruit production, grams/plant | 1400 | 1609 | 1412 |

Table 2 shows plant characteristics of the new variety compared with plant characteristics of the commercial varieties 'Driscoll Lanai' and 'San Juan'. Plant characteristics include plant height, diameter, the number of crowns per plant, habit, the density of individual plants and the vigor.

TABLE 2

| Characteristic | 'DrisStrawEleven' | 'Driscoll Lanai' | 'San Juan' |
|---|---|---|---|
| Plant height (cm) | 24.4 | 25.1 | 24.7 |
| Plant diameter (cm) | 37.5 | 36.5 | 38.9 |
| Number of crowns/plant | 3 | 3 | 3 |
| Habit | Upright | Flat globose | Globose |
| Density of individual plant | Between open and medium | Medium | Between medium and dense |
| Vigor | Strong | Medium | Medium |

Table 3 shows leaf characteristics of the new cultivar compared with leaf characteristics of 'Driscoll Lanai' and 'San Juan'. Leaf characteristics include terminal leaflet length and width in centimeters, length to width ratio, number of teeth per terminal leaflet, shape of teeth, color of upperside and underside of leaf, leaf shape in cross section, leaf blistering, leaf glossiness, number of leaflets, terminal leaflet margin, terminal leaflet length to width ratio, overall leaf shape and shape of leaf apex and base.

TABLE 3

| Leaf Characteristic | 'DrisStrawEleven' | 'Driscoll Lanai' | 'San Juan' |
|---|---|---|---|
| Terminal leaflet length (cm) | 0.76 | 0.79 | 0.74 |
| Terminal leaflet width (cm) | 0.82 | 0.76 | 0.79 |
| Terminal leaflet length/width ratio | 0.9 | 1.0 | 0.9 |
| No. teeth/ terminal leaflet | 21 | 23 | 25 |
| Shape of teeth | Rounded | Rounded | Rounded |
| Color of upper surface of leaf | RHS 147A (Dark yellow-green) | RHS 147A (Dark yellow-green) | RHS 147A (Dark yellow-green) |
| Color of lower surface of leaf | RHS 147C (Medium yellow-green) | RHS 147C (Medium yellow-green) | RHS 147B (Medium yellow-green) |
| Leaf shape in cross section | Concave | Slightly concave | Concave |
| Leaf blistering | Medium | Medium | Weak |
| Leaf glossiness | Medium | Medium | Medium |
| No. leaflets | 3 | 3 | 3 |
| Terminal leaflet margin | Cupped | Revolute | Revolute |
| Terminal leaflet: length/width ratio | As long as broad | As long as broad | As long as broad |
| Terminal leaflet shape | Orbicular | Orbicular | Orbicular |
| Terminal leaflet base shape | Rounded | Rounded | Rounded |
| Terminal leaflet apex shape | Rounded | Rounded | Rounded |

Table 4 shows information about the petiole, the petiolule, the bract, and the stipule of the new cultivar compared to 'Driscoll Lanai' and 'San Juan'. This includes petiole length in centimeters, petiole diameter in centimeters, petiole pubescence, pose of hairs on the petiole, color of the petiole, color of the petiolule, petiolule length in centimeters, petiolule diameter in centimeters, bract frequency per petiole, stipule length in centimeters, stipule width in centimeters, stipule pubescence and stipule anthocyanin coloration.

TABLE 4

| Characteristic | 'DrisStrawEleven' | 'Driscoll Lanai' | 'San Juan' |
|---|---|---|---|
| Petiole length (cm) | 11.2 | 13.6 | 11.0 |
| Petiole diameter (cm) | 0.403 | 0.389 | 0.404 |
| Petiole pubescence | Medium | Dense | Dense |
| Petiole pose of hairs | Upwards | Outwards | Upwards |
| Petiole color | RHS 145A (Medium yellow-green) | RHS 144C (Medium yellow-green) | RHS 144C (Medium yellow-green) |
| Petiolule color | RHS 145B (Medium yellow-green) | RHS 144C (Medium yellow-green) | RHS 145B (Medium yellow-green) |
| Petiolule length (cm) | 1.102 | 1.203 | 0.734 |
| Petiolule diameter (cm) | 0.202 | 0.151 | 0.177 |
| Bract frequency | 0 | 0 | 1 |
| Stipule length (cm) | 3.3 | 3.5 | 3.2 |
| Stipule width (cm) | 1.212 | 0.832 | 1.167 |
| Stipule pubescence | Medium | Dense | Dense |
| Stipule anthocyanin coloration | Absent or very weak | Absent or very weak | Absent or very weak |

Table 5 shows stolon characteristics of the new cultivar compared to 'Driscoll Lanai' and 'San Juan'. These characteristics include the number of stolons, average number of daughter plants, the anthocyanin coloration of the stolons, the thickness of the stolons, and the pubescence of the stolons.

TABLE 5

| Characteristic | 'DrisStrawEleven' | 'Driscoll Lanai' | 'San Juan' |
|---|---|---|---|
| Stolon Number | Medium | Many | Between medium and many |
| Average number of daughter plants | 42 | 17 | 57 |
| Stolon Anthocyanin | Medium | Strong | Strong |
| Stolon Thickness | Thick | Between medium and thick | Medium |
| Stolon Pubescence | Medium | Dense | Medium |

Table 6 shows inflorescence characteristics of the new cultivar compared to 'Driscoll Lanai' and 'San Juan'. These characteristics include inflorescence position relative to foliage, time of flowering, relative flower size, flower diameter in centimeters (measured from petal tip to petal tip), petal shape, relative spacing of petals, petal apex, base and margin, petal length in centimeters, petal width in centimeters, petal length to width ratio, number of petals, petal color, calyx diameter in centimeters (measured on back of flower from sepal tip to sepal tip), diameter of calyx relative to corolla, diameter of inner calyx relative to outer, sepal shape, apex and margin, sepal length in centimeters (measured from sepal tip to point of attachment to receptacle), sepal width in centimeters, number of sepals, receptacle color and anther color.

TABLE 6

| Characteristic | 'DrisStrawEleven' | 'Driscoll Lanai' | 'San Juan' |
|---|---|---|---|
| Inflorescence position relative to foliage | Beneath | Above | Above |
| Time of flowering (50% of plants at first flower) | Between early and medium | Between early and medium | Between early and medium |
| Flower size | Medium | Medium | Medium |
| Flower diameter (cm) | 2.882 | 2.835 | 2.850 |
| Petal shape | Orbicular | Orbicular | Orbicular |
| Petal spacing | Touching to overlapping | Overlapping | Overlapping |
| Petal apex shape | Rounded | Rounded | Rounded |
| Petal margin | Entire | Entire | Entire |
| Petal base shape | Concave-convex | Concave-convex | Concave-convex |
| Petal length (cm) | 1.181 | 1.133 | 1.227 |
| Petal width (cm) | 1.334 | 1.200 | 1.339 |
| Petal length/width ratio | 0.9 - As long as broad | 0.9 - As long as broad | 0.9 - As long as broad |
| Typical and observed petal number | 6 | 6 | 6 |
| Petal color | RHS 155D (White) | RHS 155B (White) | RHS 155C (White) |
| Calyx diameter (cm) | 3.307 | 3.647 | 3.969 |
| Calyx diameter relative to corolla | Smaller | Between larger and much larger | Larger |
| Inner calyx diameter relative to outer | Same size | Same size | Same size |
| Sepal shape | Elliptical | Elliptical | Elliptical |
| Sepal apex shape | Convex | Convex | Convex |
| Sepal margin | Entire | Entire | Entire |
| Sepal length (cm) | 1.131 | 1.297 | 1.330 |
| Sepal width (cm) | 0.593 | 0.560 | 1.266 |
| Typical and observed sepal number | 12 | 13 | 13 |
| Receptacle color | RHS 1A (Medium yellow-green) | RHS 150B (Medium yellow-green) | RHS 2B (Medium yellow) |
| Anther color | RHS 166A (Dark greyed-orange) | RHS N167C (Light greyed-orange) | RHS163B (Medium greyed-orange) |

Table 7 shows fruit characteristics of the new cultivar compared to 'Driscoll Lanai' and 'San Juan'. These characteristics include fruiting truss length in centimeters, fruiting truss diameter, number of berries per truss, fruiting truss attitude, fruiting truss color, fruit length in centimeters, fruit truss width in centimeters, fruit length to width ratio, fruit hollow length and width in centimeters, fruit hollow length to width ratio, fruit weight in grams, relative fruit size, predominant fruit shape, difference in shape between primary and secondary fruits, band without achenes, unevenness of fruit surface, fruit skin color, evenness of fruit color, fruit glossiness, insertion of achenes, achene coloration (sunward and shaded sides of berry) and the number of achenes per berry.

TABLE 7

| Characteristic | 'DrisStrawEleven' | 'Driscoll Lanai' | 'San Juan' |
|---|---|---|---|
| Fruiting truss length (cm) | 18.0 | 22.2 | 25.1 |

TABLE 7-continued

| Characteristic | 'DrisStrawEleven' | 'Driscoll Lanai' | 'San Juan' |
|---|---|---|---|
| Fruiting truss length-general | Medium | Long | Long |
| Fruiting truss diameter (cm) | 0.551 | 0.360 | 0.481 |
| Number of berries per fruiting truss | 3 | 4 | 4 |
| Fruiting truss attitude | Semi-erect | Semi-erect | Semi-erect |
| Fruiting truss color at base of truss | RHS 144A (Medium yellow-green) | RHS 144A (Medium yellow-green) | RHS 144A (Medium yellow-green) |
| Fruit length (cm) | 4.233 | 4.327 | 4.857 |
| Fruit width (cm) | 3.930 | 4.431 | 4.603 |
| Fruit length/width ratio | 1.1 | 1.0 | 1.1 |
| Fruit hollow length (cm) | 1.971 | 2.055 | 2.169 |
| Fruit hollow width (cm) | 1.190 | 0.774 | 0.738 |
| Fruit hollow length/width ratio | 1.7 | 2.7 | 2.9 |
| Fruit weight (g) | 24.5 | 25.6 | 28.0 |
| Relative fruit size | Medium | Medium | Large |
| Predominant fruit shape | Conical | Conical | Conical |
| Difference in shape between primary & secondary fruits | Slight | Slight | Slight |
| Band without achenes | Narrow | Narrow | Narrow |
| Unevenness of fruit surface | Between weak and medium | Between medium and strong | Medium |
| Fruit skin color | RHS 46A (Dark red) | RHS 46A (Dark red) | RHS 53A (Dark red) |
| Evenness of fruit color | Even | Even | Even |
| Fruit glossiness | Between medium and strong | Medium | Between medium and strong |
| Insertion of achenes | Level with surface | Above surface | Below surface |
| Achene coloration - sunward side of berry | RHS 183A (Dark greyed-purple) | RHS 183C (Dark greyed-purple) | RHS 180B (Medium greyed-red) |
| Achene coloration shaded side of berry | RHS 180B (Medium greyed-red) | RHS 152B (Medium yellow-green) | RHS 150B (Light yellow-green) |
| Achenes per berry | 278 | 345 | 397 |

Table 8 shows fruit characteristics of the new cultivar compared to 'Driscoll Lanai' and 'San Juan'. These characteristics include the harvest maturity, insertion of calyx, pose of calyx segments, size of calyx in relation to fruit, adherence of calyx, firmness of flesh, color of the fruit flesh, evenness of the flesh color, distribution of flesh color, hollow center, sweetness of fruit, acidity of fruit, texture of fruit when tasted, type of bearing, grams of fruit per plant.

TABLE 8

| Characteristic | 'DrisStrawEleven' | 'Driscoll Lanai' | 'San Juan' |
|---|---|---|---|
| Harvest maturity | Late March to early November | Late March to early November | Late March to early November |
| Insertion of calyx | Level | Level | Level |

TABLE 8-continued

| Characteristic | 'DrisStrawEleven' | 'Driscoll Lanai' | 'San Juan' |
|---|---|---|---|
| Pose of calyx segments | Spreading | Reflexed | Reflexed |
| Size of calyx in relation to fruit | Larger | Larger | Between smaller and same size |
| Adherence of calyx | Strong | Medium | Strong |
| Firmness of flesh | Firm | Medium | Firm |
| Color of the flesh | RHS 44B (Medium red) and RHS N155C (white) | RHS 41B (Medium red) and RHS 155A white | RHS 41A (Medium red) and RHS 155B white |
| Evenness of flesh color | Uneven | Slightly uneven | Slightly uneven |
| Distribution of flesh color | Marginal and central | Marginal and central | Marginal and central |
| Hollow center | Small | Medium | Small |
| Sweetness | Strong | Medium | Strong |
| Acidity | Medium | Medium | Weak |
| Texture when tasted | Coarse | Medium | Fine |
| Type of bearing | Partially everbearing | Partially everbearing | Partially everbearing |
| Grams of fruit/plant | 1400 | 1609 | 1412 |

Table 9 shows pest and disease characteristics of the new cultivar compared to 'Driscoll Lanai' and 'San Juan'.

TABLE 9

| Pest, Stress or Disease | 'DrisStrawEleven' | 'Driscoll Lanai' | 'San Juan' |
|---|---|---|---|
| *Tetranychus urticae* | Susceptible | Susceptible | Moderately usceptible |
| *Botrytis* fruit rot | Moderately susceptible | Susceptible | Susceptible |
| Powdery mildew | Susceptible | Susceptible | Susceptible |
| *Verticillium* wilt | Susceptible | Moderately susceptible | Susceptible |
| Strawberry mottle virus | Moderately resistant | Moderately resistant | Moderately resistant |
| *Xanthomonas fragariae* | Moderately susceptible | Moderately susceptible | Moderately susceptible |

COMPARISON WITH PARENTAL AND COMMERCIAL CULTIVARS

When 'DrisStrawEleven' is compared to the proprietary female parent '122J81' (unpatented), 'DrisStrawEleven' has larger fruit than '122J81'. Additionally, 'DrisStrawEleven' is partially everbearing, while '122J81' is everbearing.

When 'DrisStrawEleven' is compared to the proprietary male parent '111H69' (unpatented), 'DrisStrawEleven' has smaller fruit and has a lower chilling requirement than '111H69'.

We claim:

1. A new and distinct cultivar of strawberry plant as described and shown herein.

* * * * *